(12) United States Patent
Rodriguez-Kabana et al.

(10) Patent No.: US 7,462,579 B2
(45) Date of Patent: Dec. 9, 2008

(54) 2-BUTENAL, TRANS-2-PENTENAL AND RELATED ENAL COMPOUNDS FOR CONTROLLING PLANT PESTS AND WEEDS IN SOIL

(75) Inventors: Rodrigo Rodriguez-Kabana, Auburn, AL (US); Elizabeth A. Guertal, Auburn, AL (US); Robert H. Walker, Auburn, AL (US); David H. Teem, Auburn, AL (US)

(73) Assignee: Auburn University, Auburn, AL (US)

( * ) Notice: Subject to any disclaimer, the term of this patent is extended or adjusted under 35 U.S.C. 154(b) by 216 days.

(21) Appl. No.: 11/260,771

(22) Filed: Oct. 27, 2005

(65) Prior Publication Data

US 2006/0089263 A1    Apr. 27, 2006

Related U.S. Application Data

(60) Provisional application No. 60/622,460, filed on Oct. 27, 2004.

(51) Int. Cl.
*A01N 35/02* (2006.01)
(52) U.S. Cl. .................................. 504/348; 514/703
(58) Field of Classification Search ............... 504/348; 514/703
See application file for complete search history.

(56) References Cited

U.S. PATENT DOCUMENTS

| | | | | |
|---|---|---|---|---|
| 3,028,304 A | * | 4/1962 | Kreutzer | ............... 514/703 |
| 4,851,583 A | * | 7/1989 | Bockowski et al. | ......... 568/465 |
| 5,866,614 A | | 2/1999 | Bockowski et al. | |
| 6,294,584 B1 | * | 9/2001 | Bockowski et al. | ......... 514/693 |

FOREIGN PATENT DOCUMENTS

JP    55-2616    *    1/1980

OTHER PUBLICATIONS

HCAPLUS abstract 1998:65272 (1998).*
JPAB abstract JP355002616A, abstracting JP 55-2616 (1980).*
Derwent abstract 1980-11988C, abstracting JP 55-2616 (1980).*
Enclyclopedia of Agrochemicals, John Wiley & Sons, New York, 2003, vols. 1-3, p. 1109; Retrieved online on Jan. 15, 2008 from <www.knovel.com>.*
English translation of JP 55002616 (Jan. 1980).*

* cited by examiner

*Primary Examiner*—John Pak

(57) ABSTRACT

A method for controlling pests and weeds on or around plants, especially crop plants is disclosed. The method includes admixing 2-butenal, trans-2-pentenal or other related enal compounds to form an aqueous solution, and applying the aqueous solution to plants, plant seeds, weeds, or soil around the around the area in which the plants grow.

7 Claims, 10 Drawing Sheets

FIGURE 2. GROWTH RESPONSE OF 'YOUNG' SOYBEAN TO PRE-PLANT APPLICATIONS OF 2-PROPENAL [ACROLEIN] IN AN EXPERIMENT WITH SOIL FROM A COTTON FIELD INFESTED WITH THE RENIFORM NEMATODE [ROTYLENCHULUS RENIFORMIS]

FIGURE 4. CONTROL OF YELLOW NUTSEDGE WITH POST-EMERGENCE APPLICATIONS OF 2-PROPENAL IN AN EXPERIMENT WITH SOIL FROM A COTTON FIELD ARTIFICIALLY INFESTED WITH THE WEED.

2-BUTENAL, TRANS-2-PENTENAL AND RELATED ENAL COMPOUNDS FOR CONTROLLING PLANT PESTS AND WEEDS IN SOIL

CROSS REFERENCE TO RELATED APPLICATION(S)

This application claims priority to U.S. Provisional Application No. 60/622,460, filed Oct. 27, 2004.

BACKGROUND OF THE INVENTION

The present invention relates to pesticides and herbicides, and more particularly to the use of 2-propenal and related enal compounds for controlling pests and weeds on or around plants, especially crop plants.

A variety of herbicides are well known and have been long used to kill unwanted weeds in crop fields. Typically, these herbicides are sprayed onto the soil (pre-emergence), or onto the plants themselves (post-emergence). Pesticides are also well known, and are necessary for reducing the level of pest infestation in the soil around the area in which the plants grow or on the plants themselves. One such pesticide is methyl bromide. Methyl bromide is an odorless, colorless gas that has been used as an agricultural soil fumigant to control a wide variety of pests. However, because it has been discovered that methyl bromide depletes the stratospheric ozone layer, its use is being phase out. It is therefore desirable to find a replacement for methyl bromide.

It is well known that many herbicides and pesticides are expensive, quite toxic to the environment, and often times result in unintended consequences such as soil and ground water contamination, crop damage, spray drift on non-targeted plant species, and other health concerns. It is therefore desirable to provide an active compound that is relatively inexpensive, is less toxic to the environment, and minimizes the unintended consequences noted above, yet remains effective against weeds and pests.

Herbicides and pesticides also have a further disadvantage in that the active ingredient, as well as being quite toxic, has no function other than killing weeds or pests. In other words, the active ingredient typically does not have any beneficial effect on the soil or for the plant. Thus, it would also be desirable to provide an active ingredient that is not only herbicidally and pesticidally effective, but also may have some beneficial effect on plant growth.

SUMMARY OF THE INVENTION

The present invention is directed toward the use of 2-propenal and related enal compounds for controlling pests and weeds on or around plants, particularly crop plants. In one embodiment, the invention is directed toward a method for controlling pests and weeds on or around plants comprising the steps of providing as an active compound an olefinically unsaturated lower alkyl aldehyde having the formula

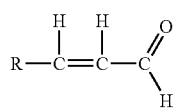

where R may be hydrogen or a straight chain alkyl radical having 1 to 5 carbon atoms, admixing an effective amount of the active compound with water to form an aqueous solution, and applying the aqueous solution to plants, plant seeds, weeds or soil around the area in which the plants grow. The preferred compounds are 2-propenal (acrolein), 2-butenal (crotonaldehyde) and trans-2-pentenal.

Although the application of these enal compounds are herbicidally and pesticidally effective with all types of plants, they are particularly effective when used to control pests and weeds on or around crop plants. Typical crop plants include corn, wheat, barley, oats, rice, sorghum, cotton, soybeans, potatoes, strawberries, tomatoes, sunflowers, sugar beets, oilseeds, peppers, turnips, turf and cabbage. The above list is not all-inclusive, and only represents but a few of the crop plants with which the active enal compounds disclosed herein can be used.

The active enal compound is admixed with water in an amount of from about 1 to about 1350 parts of the active compound per million parts of water. Typically, the water will comprise irrigation water for the above crop plants. Typical application rates are from about 75 pounds to about 800 pounds of the active compound per acre of soil, and preferably the active is drenched in the soil to a depth of about 10 to about 12 inches to provide effective and long lasting herbicidal and pesticidal activity.

In another embodiment of the invention, it has been unexpectedly found that in low doses, the enal compounds disclosed herein provide a method of enhancing growth of the plants, especially crop plants. It has been discovered that the application of the active compound to soil around the area in which the plants grow in an amount of from about 1 pound to about 600 pounds of said active compound per acre of soil (lbs/A), preferably from about 100 to about 400 lbs/A, results in increased growth of plants as compared to plants growing in untreated soils.

In yet another embodiment of the present invention, it has further been unexpectedly found that the application of the active ingredient to soil around the area in which tomato plants grow results in reduced transplant shock of the tomato plants.

DETAILED DESCRIPTION OF THE INVENTION

Figure 1A:
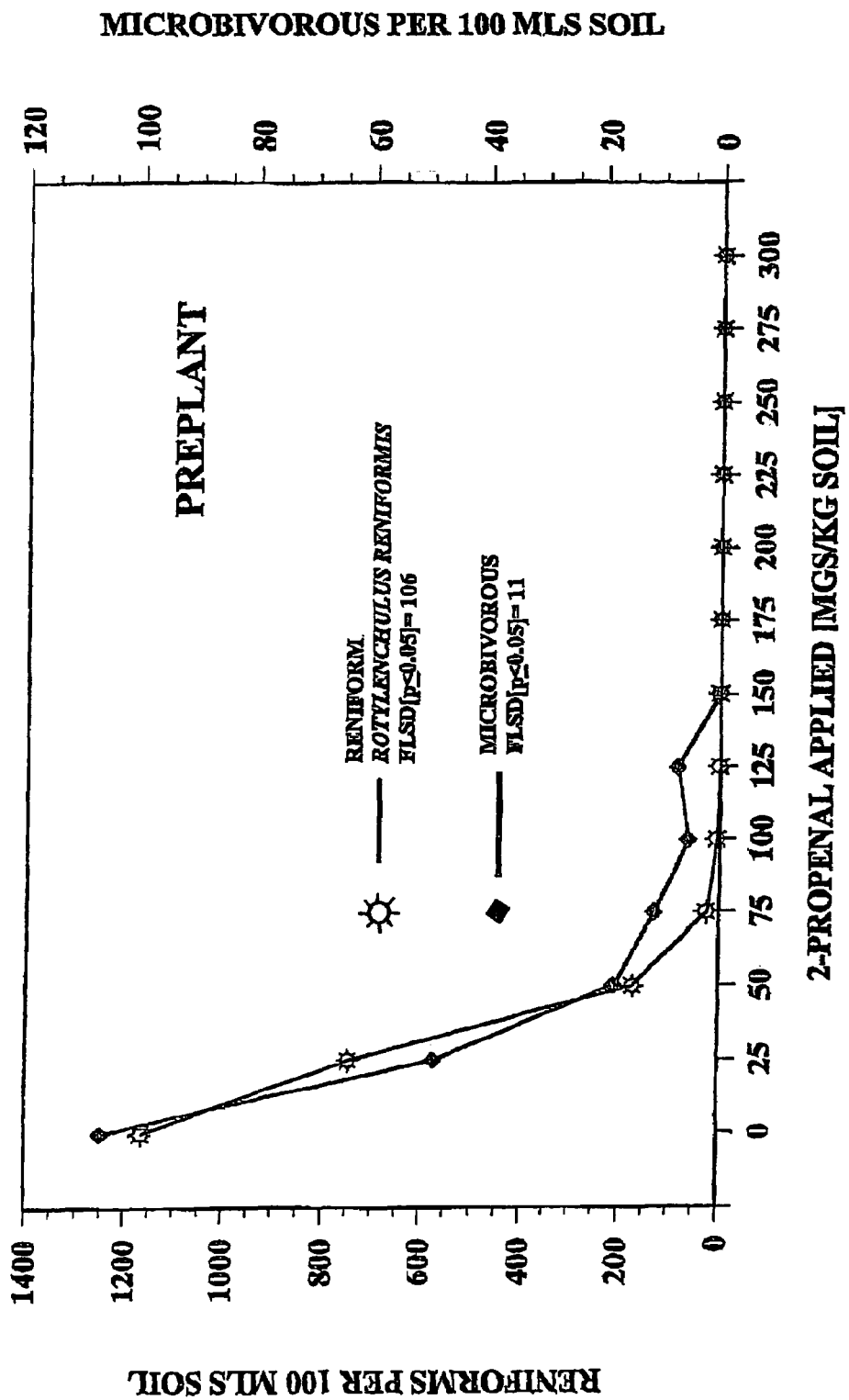
FIG. 1A is a graph illustrating the effect of 2-propenal on reniform and microbivorous nematodes in soil at various pre-emergent application rates.

It has now been discovered that the addition of olefinically unsaturated lower alkyl aldehydes to water, particularly irrigation water, employed in the agricultural industry for growing plants, especially crop plants, destroys and kills, or at least effectively inhibits, and therefore controls pests and weeds on or around such plants, without adversely affecting the plants themselves. Thus, the use of these olefinically unsaturated lower alkyl aldehydes in the amounts hereinafter described, kills, destroys and/or inhibits the growth of pests and weeds for substantial periods of time without affecting to any material degree the plant itself. These aldehydes thus provide an effective replacement for methyl bromide.

The olefinically unsaturated lower alkyl aldehydes contemplated by the present invention for use as the pesticidally and herbicidally effective active compound are those represented by the following general formula

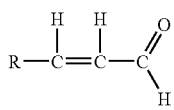

where R may be hydrogen or a straight chain alkyl radical having 1-5 carbon atoms. The preferred active compounds are 2-propenal (acrolein) having the structure

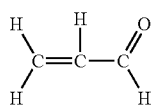

or 2-butenal (crotonaldehyde) having the structure

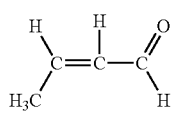

or trans-2-pentenal having the structure

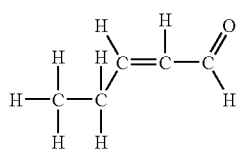

The most preferred active compound is 2-propenal which, as noted above, is commonly referred to as acrolein.

The above aldehydes are commercially available or can be synthesized by methods well known in the art. For example, 2-propenal is available under the trade name "MAGNACIDE H" from Baker Petrolite. It may be commercially prepared by vapor phase oxidation of propylene wth air or oxygen in the presence of a catalyst. Reference should be made to Shell Oil Company's U.S. Pat. No. 2,042,220 for a description of the synthesis. 2-butenal is available under the trade name "crotonaldehyde" from Richmond Chemical, Inc. Trans-2-pentenal is available from Nanyang Chemicals and China Aroma Chemicals Co., Ltd.

The rate of application of the active ingredient will depend on a number of factors including, for example, the extent of the herbicidal and pesticidal activity of the active ingredient, the plant species with which the active ingredient is to be used, the growth stage of the plant, the method of application, the weed and/or pest to be eliminated, and the time period of effectiveness desired, among other factors. As a general guide, however, the application rate of the active ingredient is from about 75 pounds to about 800 pounds of the active compound per acre of soil. For pest control, typical application rates will be about 75 pounds to about 300 pounds per acre of soil, and most preferably about 100 to about 200 pounds of active per acre of soil. For weed control, the application rate is preferably about 200 to about 800 pounds of active per acre of soil, and most preferably about 200 to about 400 pounds of active per acre of soil.

The preferred method of application is addition of the active ingredient to irrigation water. This is typically accomplished by attaching a container of the active ingredient to an irrigation line through a control valve. As irrigation water moves through the irrigation pipe, it draws the active ingredient from its container to be admixed therewith to form the aqueous solution to be applied to the plants, plant seeds, weeds or soil around the area in which the plants grow. The amount of active ingredient is metered by the control valve, or other conventional means. Preferably, to be most effective, the aqueous solution containing the active ingredient should be allowed to drench the soil on which it is applied to a depth of about 10 to about 12 inches. Drenching to this depth will enable the active compound to be herbicidally and pesticidally effective for a longer period of time. However, drenching is not required, but is only preferred. The effective amount of the active ingredient admixed with the irrigation water to form the aqueous solution will typically be from about 1 to about 1350 parts of the active compound per million parts of water. Preferably, the concentration of active in the aqueous solution is from about 300 parts to about 1300 parts of the active compound per million parts of water.

Spraying of the aqueous solution containing one or more active enal compounds is not recommended. The enal compounds disclosed herein are very volatile and hydrophilic. As such, attempting to apply these active ingredients via spraying would result in high evaporation rates of the active compound to the extent that spraying reduces the amount of active ingredient actually applied to the plant, plant seeds, weeds or soil so that this technique is substantially ineffective in controlling pests and weeds.

The aqueous solution containing the active ingredient applied to plants, plant seeds, weeds or soil around the area in which the plants grow, may also contain other adjuvants commonly utilized in agricultural compositions. Such adjuvants include compatibilizing agents, anti-foam agents, sequestering agents, neutralizing agents, buffers, corrosion inhibitors, dyes, odorants, spreading agents, penetration aids, sticking agents, dispersing agents, thickening agents, freezing point depressants, antimicrobial agents, ultraviolet (UV)

light absorbers, and the like. The compositions may also contain other compatible components, for example, other herbicides or pesticides, plant growth regulants, fungicides, insecticides, and the like. The active ingredients can also be formulated together with liquid or solid fertilizers such as ammonium nitrate, urea, and the like.

Representative plant species that may be treated with the active enal compounds of the present invention include domestic and agricultural plants, especially crop plants such as corn, wheat, barley, oats, rice, sorghum, cotton, soybeans, potatoes, strawberries, tomatoes, sunflowers, sugar beets, oilseeds, peppers, turnips, turf and cabbage. It should be particularly noted that it is not intended that the use of these active enal compounds and the methods of the present invention be limited only to the above listed plant species. The active ingredient and the method disclosed herein is effective for controlling pests and weeds on or around all plant species.

It will be understood by one skilled in the art that the adjuvants listed above are not essential to the activity of the active enal compounds. Their proportions, therefore, are not critical and may be optimized for the purpose and method of application by one skilled in the art. It should also be apparent to one skilled in the art that the adjuvants listed above may be used alone or in combination with one or more of the active enal compounds of the present invention.

In addition, it will also be apparent to one skilled in the art that the active enal compounds of the present invention may be used singly (alone), in combination with one or more other active enal compounds, or with one or more other auxiliary herbicides and/or pesticides. Such auxiliary pesticides may be a chemical pesticide, a fungal insecticide, a viral insecticide or a biopesticide such as a Bacillus-based insecticide.

The chemical pesticide may be selected from carbamates, avermectins, insect growth regulators, pyroles, organophosphates, pyrazoles, chlorinated arganics or pyrethroids. The viral insecticide may be a polyhedrosis or a granulosis virus.

Examples of biopesticides include but are not limited to baculoviruses, such as nuclear polyhedrosis virus (NPV), e.g. *Autographa califomica* NPV, *Syngrapha falcifera* NPV, *Heliothis zea* NPV, *Lymantria dispar* NPV, *Spodoptera exigua* NPV, *Neodiprion lecontei* NPV, *Neodiprion sertifer* NPV, *Harrisina brillians* NPV, *Endopiza viteana* Clemens NPV; granulosis viruses e.g., *Cydia pomonella* granulosis virus (GV), *Pieris brassicae* GV, *Pieris rapae* GV; entomopathogenic fungi, such as *Beauveria bassiana*, *Metarhizium anisopliae*, *Verticillium lecanii*, and *Paecilomyces* spp. and various *Bacillus*-based products. Examples of *Bacillus*-related pesticides include but are not limited to pesticides produced by *Bacillus thuringiensis* subsp. *kurstaki*, *Bacillus thuringiensis* subsp. *aizawai*, *Bacillus thuringiensis* subsp. *israelensis*, *Bacillus thuringiensis* subsp. *tenebrionis*, *Bacillus sphaericus*, *Bacillus cerius*, *Bacillus thuringiensis* kurstaki/tenebrionis, *Bacillus thuringiensis* aizawai/kurstaki, and *Bacillus thuringiensis* kurstaki/kurstaki.

The abovementioned pests which can be controlled by the method according to the invention include, for example, insects, representatives of the order acarina and representatives of the class nematoda; especially from the order *Lepidoptera Acleris* spp., *Adoxophyes* spp., especially *Adoxophyes reticulana; Aegeria* spp., *Agrotis* spp., especially *Agrotis spinifera; Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., especially *Cydia pomonella*; *Diatraea* spp., *Diparopsis castanea*, *Earias* spp., *Ephestia* spp., especially *E. Khuniella*; *Eucosma* spp., *Eupoecilia ambiguella*, *Euproctis* spp., *Euxoa* spp., *Grapholita* spp., *Hedya nubiferana*, *Heliothis* spp., especially *H. virescens* and *H. zea*; *Hellula undalis*, *Hyphantria cunea*, *Keiferia lycopersicella*, *Leucoptera scitella*, *Lithocollethis* spp., *Lobesia* spp., *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora* spp., *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera littoralis*, *Synanthedon* spp., *Thaumetopoea* spp., *Tortrix* spp., *Trichoplusia ni* and *Yponomeuta* spp.; from the order Coleoptera, for example *Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Oryzaephilus* spp., *Otiorhynchus* spp., *Phlyctinus* spp., *Popillia* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.; from the order Orthoptera, for example *Blatta* spp., *Blattella* spp., *Gryllotalpa* spp., *Leucophaea maderae*, *Locusta* spp., *Periplaneta* spp. and *Schistocerca* spp.; from the order Isoptera, for example *Reticulitermes* spp.; from the order Psocoptera, for example *Liposcelis* spp.; from the order Anoplura, for example *Haematopinus* spp., *Linognathus* spp., *Pediculus* spp., *Pemphigus* spp. and *Phylloxera* spp.; from the order Mallophaga, for example *Damalinea* spp. and *Trichodectes* spp.; from the order Thysanoptera, for example *Frankliniella* spp., *Hercinothrips* spp., *Taeniothrips* spp., *Thrips palmi*, *Thrips tabaci* and *Scirtothrips aurantii*; from the order Heteroptera, for example *Cimex* spp., *Distantiella theobroma*, *Dysdercus* spp., *Euchistus* spp. *Eurygaster* spp. *Leptocorisa* spp., *Nezara* spp., *Piesma* spp., *Rhodnius* spp., *Sahlbergella singularis*, *Scotinophara* spp. and *Triatoma* spp.; from the order Homoptera, for example *Aleurothrixus floccosus*, *Aleyrodes brassicae*, *Aonidiella aurantii*, *Aphididae*, *Aphiscraccivora*, *A. fabae*, *A. gosypii*; *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma lanigerum*, *Erythroneura* spp., *Gascardia* spp., *Laodelphax* spp., *Lecanium corni*, *Lepidosaphes* spp., *Macrosiphus* spp., *Myzus* spp., especially *M. persicae*; *Nephoteffix* spp., especially *N. cincticeps*; *Nilaparvata* spp., especially *N. lugens*; *Paratoria* spp., *Pemphigus* spp., *Planococcus* spp., *Pseudaulacaspis* spp., *Pseudococcus* spp., especially *P. Fragilis*, *P. citriculus* and *P. comstocki*; *Psylla* spp., especially *P. pyri*; *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*; from the order Hymenoptera, for example *Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.; from the order Diptera, for example *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.; from the order Siphonaptera, for example *Ceratophyllus* spp. and *Xenopsylla cheopis;* from the order Thysanura, for example *Lepisma saccharina* and from the order Acarina, for example *Acarus siro, Aceria sheldoni; Aculus* spp., especially *A. schlechtendali; Amblyomma* spp., *Argas* spp., *Boophilus* spp., *Brevipalpus* spp., especially *B. californicus* and *B. phoenicis; Bryobia praetiosa, Calipitrimerus* spp., *Chorioptes* spp., *Dermanyssus gallinae, Eotetranychus* spp., especially *E. carpini* and *E. orientalis; Eriophyes* spp., especially *E. vitis; Hyalomma* spp., *Ixodes* spp., *Olygonychus pratensis, Omithodoros* spp., *Panonychus* spp., especially *P. ulmi* and *P. citri; Phyllocoptruta* spp., especially *P. oleivora; Polyphagotarsonemus* spp., especially *P. latus; Psoroptes* spp., *Rhipicephalus* spp., *Rhizoglyphus* spp., *Sarcoptes* spp., *Tarsonemus* spp. and *Tetranychus* spp., in particular *T. urticae, T. cinnabarinus* and *T. Kanzawai;* representatives of the class Nematoda; (1) nematodes selected from the group consisting of root knot nematodes, cyst-forming nematodes, stem eelworms and foliar nematodes; (2) nematodes selected from the group consisting of *Anguina* spp.; *Aphelenchoides* spp.; *Ditylenchus* spp.; *Globodera* spp., for example *Globodera rostochiensis; Heterodera* spp., for example *Heterodera avenae, Heterodera glycines, Heterodera schachtii* or *Heterodera trifolii; Longidorus* spp.; *Meloidogyne* spp., for example *Meloidogyne incognita* or *Meloidogyne javanica; Pratylenchus,* for example *Pratylenchus neglectans* or *Pratylenchus penetrans; Radopholus* spp., for example *Radopholus similis; Trichodorus* spp.; *Tylenchulus,* for example *Tylenchulus semipenetrans;* and *Xiphinema* spp.; or (3) nematodes selected from the group consisting of *Heterodera* spp., for example *Heterodera glycines;* and *Meloidogyne* spp., for example *Meloidogyne incognita.*

The method according to the invention allows pests of the abovementioned type to be controlled, i.e. contained or destroyed, which occur, in particular, on plants, mainly useful crop plants and ornamentals in agriculture, in horticulture and in forests, or on parts, such as fruits, flowers, foliage, stalks, tubers or roots, of such plants. The protection against these pests in some cases even extends to plant parts which form at a later point in time.

The above-mentioned weeds which can be controlled by the method according to the present invention include, for example, the following:

yellow nutsedge (*Cyperus esculentus*)
  purple nutsedge (*Cyperus rotundus*)
  bermudagrass (*Cynodon dactylon*)
  torpedograss (*Panicum repens*)
  morningglory (*Ipomoea* spp.)
  pigweed (*Amaranthus* spp.)
  crabgrass (*Digitaria* spp.)
  goosegrass (*Eleusine indica*)
  junglerice (*Echinochloa colonum*)
  broadleaf signalgrass (*Urochloa platphylla*)
  Texas panicum (*Panicum texanum*)
  sicklepod (*Senna obtusifolia*)
  jimson weed (*Datura stramonium*)
  foxtail (*Setaria* spp.)
  prickly sida (*Sida Spinosa*)
  small-flower morningglory *Jacquemontia tamnifolia*)
  henbit (*Lamium amplexicaule*)
  wild radish (*Rhapanus rhaphanistrum*)

The above list is not all-inclusive but only provides many of the more common weeds against which the active enal compounds are effective.

EXAMPLE 1

Methods and Materials

The nematicidal properties of 2-propenal ($CH_2=CH-CHO$; acrolein), 2-butenal ($CH_3-CH=CH-CHO$; crotonaldehyde), and trans 2-pentenal ($CH_3-CH_2-CH=CH-CHO$) were studied in greenhouse experiments with soil severely infected with the reniform nematode (*Rotylenchulus reniformis*). The soil was collected from a cotton field and was a sandy loam with pH 6.2, organic matter content <1.0% and cation exchange capacity <10 meq/100 gms soil. The soil was mixed 50:50 by volume, with washed fine siliceous river sand and the mixture, here-from referred to as soil. The moist soil (50% field capacity) was apportioned in 1 Kg quantities contained in 4L polyethylene bags. The compounds were applied to the soil in the bags, and after thorough mixing the treated soil was transferred to 1 L capacity, 4-inch-diam. plastic (PVC) pots which were then covered with a polyethylene bag (1 mil) held tightly to the outside wall of the pot with a rubber band. The covered pots were placed on a greenhouse table and after 10 days the bags were removed and soil samples for nematode analyses were collected from each pot. The pots were planted with "Young" soybean (5 seed/pot.) Soybean plants were grown for 8 weeks when they were removed, soil samples taken for nematode analysis (salad bowl incubation technique), and data were collected on shoot height, and fresh weights of shoots and roots. The relative health of the root systems was determined using a subjective scale. In the scale values ranged from 1 to 5, a value of 1 corresponded to healthy, well develop and clean looking root systems without necrotic area and no disease symptoms; a value of 5 represented roots with severely reduced development and obvious disease symptoms including large portions with necrotic and/or rotten tissue. Values between 1 and 5 represented intermediate degrees of damage. The roots were incubated to assess nematode populations in them.

Herbicidal properties of the compounds were studied as described for experiments on nematicidal activities. The soil was from a cotton field with a silt loam soil from a cotton field with similar properties as the one used for the nematode experiments. It was infested with a variety of weeds and was artificially seeded with 5 yellow nutsedge tubercles/pot. Nutsedge plants and other weeds were grown for a month, and the pots were then treated with 2-propenal and covered with polyethylene bags for 10 days, when the bags were removed and weed counts taken at two weeks and one month after treatment. Rates used in these experiments were: 0, 100, 200, 300, 400, 500, 600, 700, and 800 mgs/kg soil.

Emulsifiable concentrates (EC's) were prepared for all three compounds containing 10% (w/w) emulsogen. The EC's were used to make aqueous emulsions containing 2.5% active ingredient; these emulsions were then used to deliver the compounds to soil. Each compound was delivered using the following rates: 0, 25, 50, 75, 100, 125, 150, 175, 200, 225, 250, 275, 300 mgs/kg soil. In every experiment there were 6 replications (pots) per treatment arranged in a randomized complete block design.

All data were analyzed according to standard procedures for analysis of variance. Fisher's Least Significant Differences (FLSD) were calculated when F values were significant and are included in the graphs. Curvilineal analyses were conducted according to standard procedures with the Table-Curve 2D program.

Results

Figure 1B:
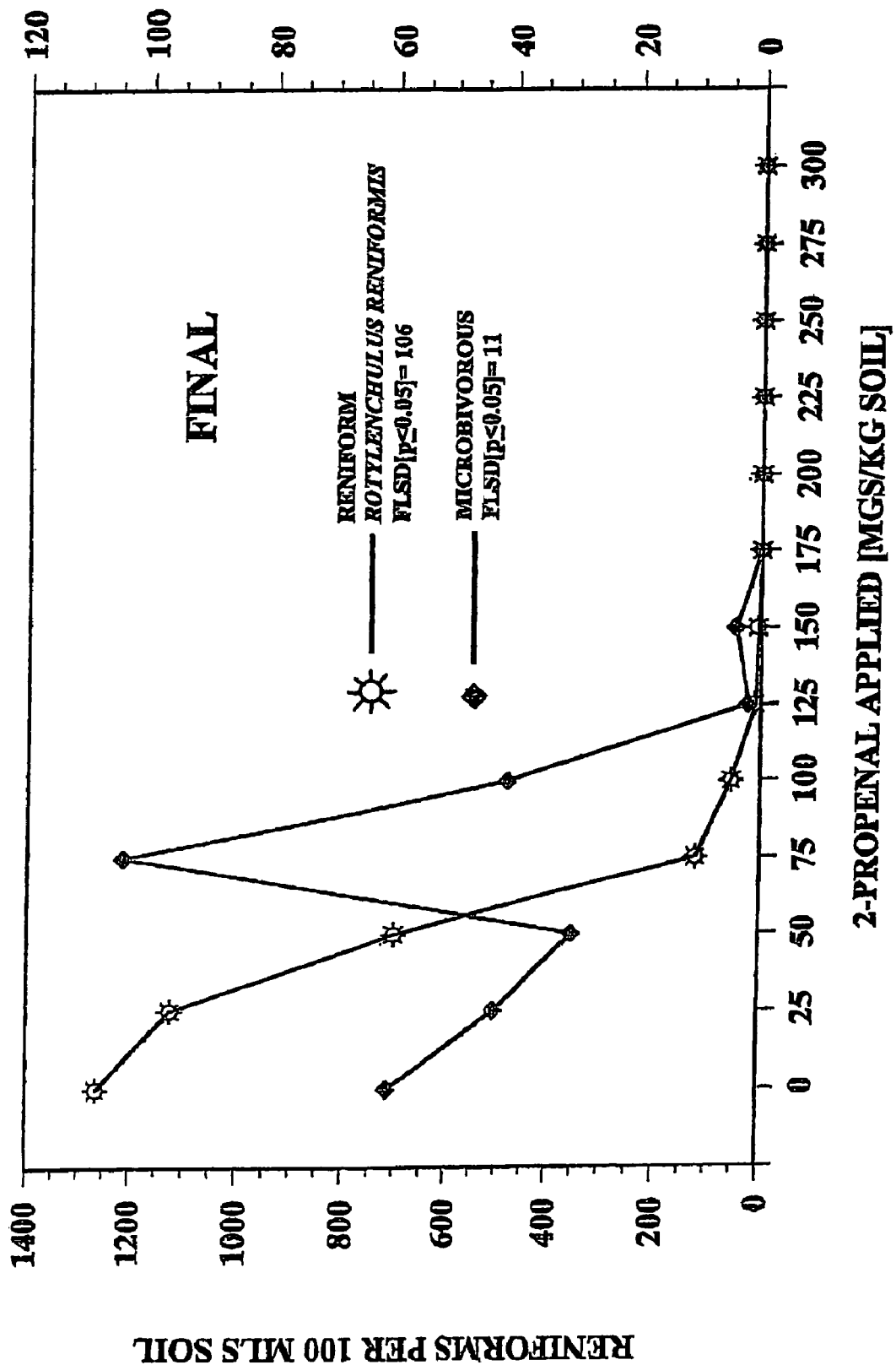
FIG. 1B is a graph illustrating the effect of 2-propenal on reniform and microbivorous nematodes in soil at termination of experiment.
Figure 1C:
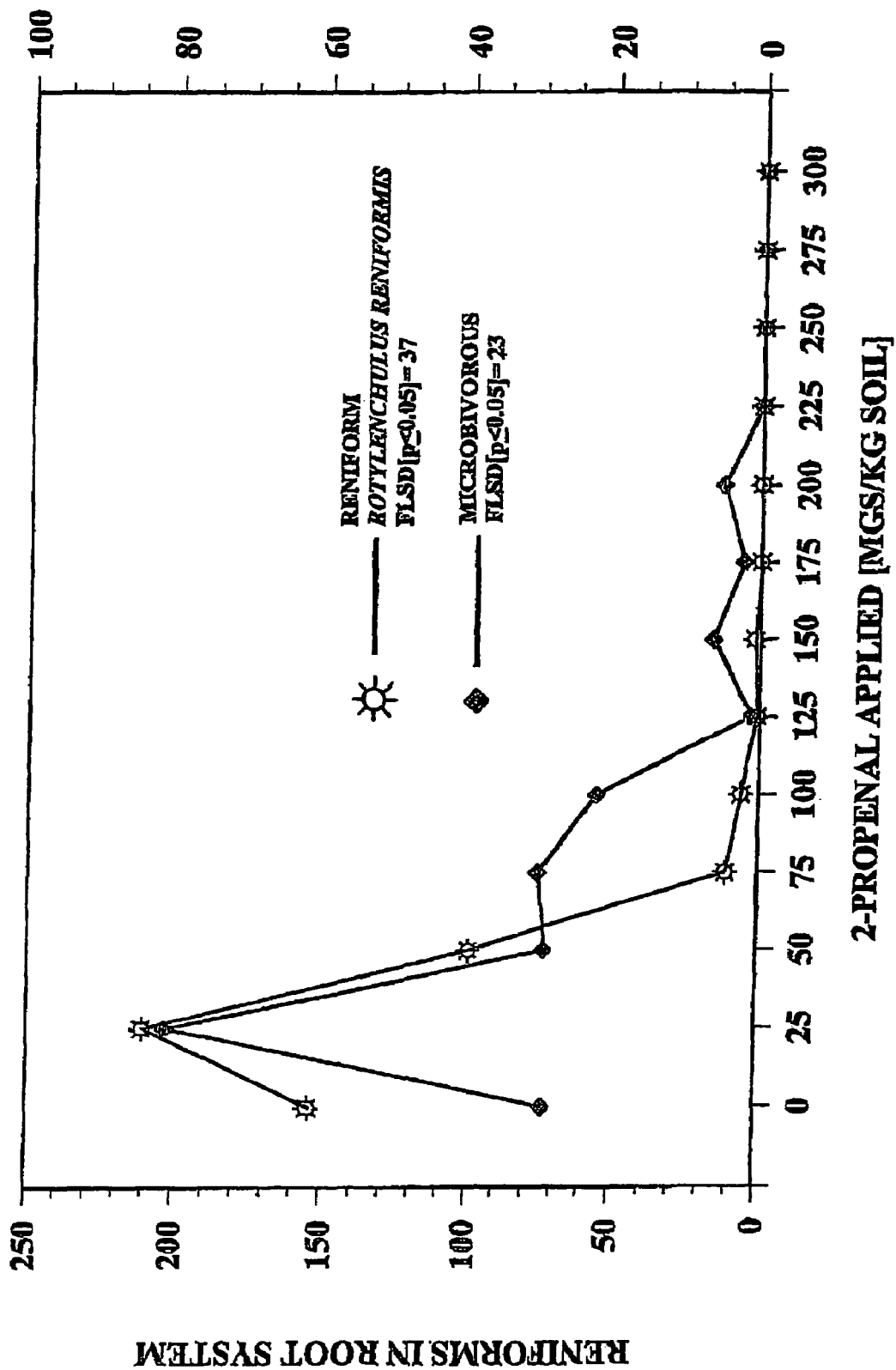
FIG. 1C is a graph illustrating the effect of 2-propenal on reniform and microbivorous populations in plant root systems at termination of experiment.

Nematicidal Activity, 2-propenal. Data obtained from the experiment with 2-propenal are presented in FIGS. 1A-1E and 2A-2E. The compound reduced exponentially populations of reniform and microbivorous nematodes in pre-plant samples (FIGS. 1A-1B). A dose of 50 mgs/kg soil equivalent to 100 lbs/A resulted in >90% reduction in these populations. Soil and root samples at the end of the pre-plant samples; however, microbivorous populations had recovered in response to applications of ≦100 mgs/kg soil and were even stimulated by the 75 mg rate.

Figure 2A:
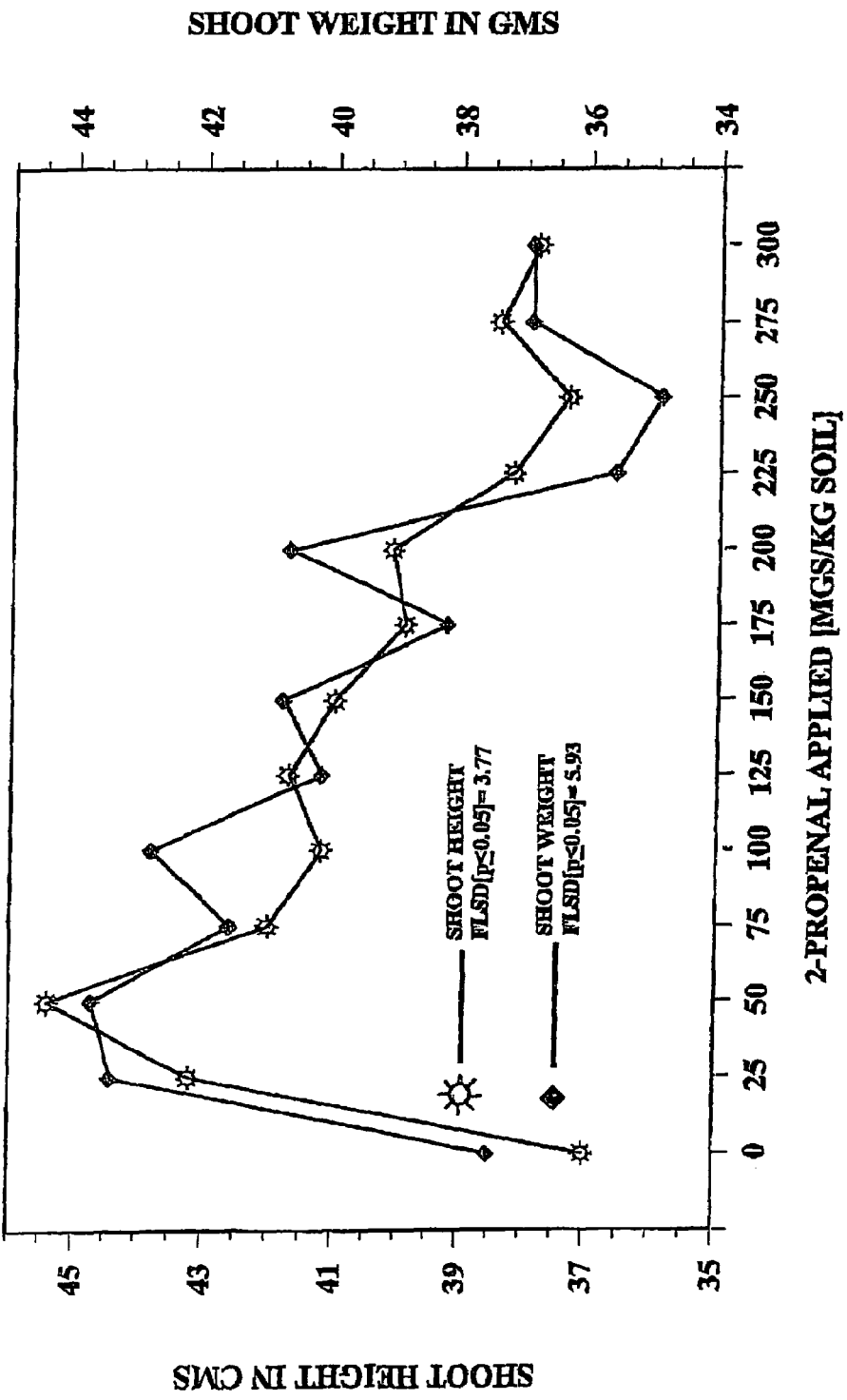
FIG. 2A is a graph illustrating the effect of 2-propenal on the growth response of young soybean plants at various pre-emergent application rates.
Figure 2B:
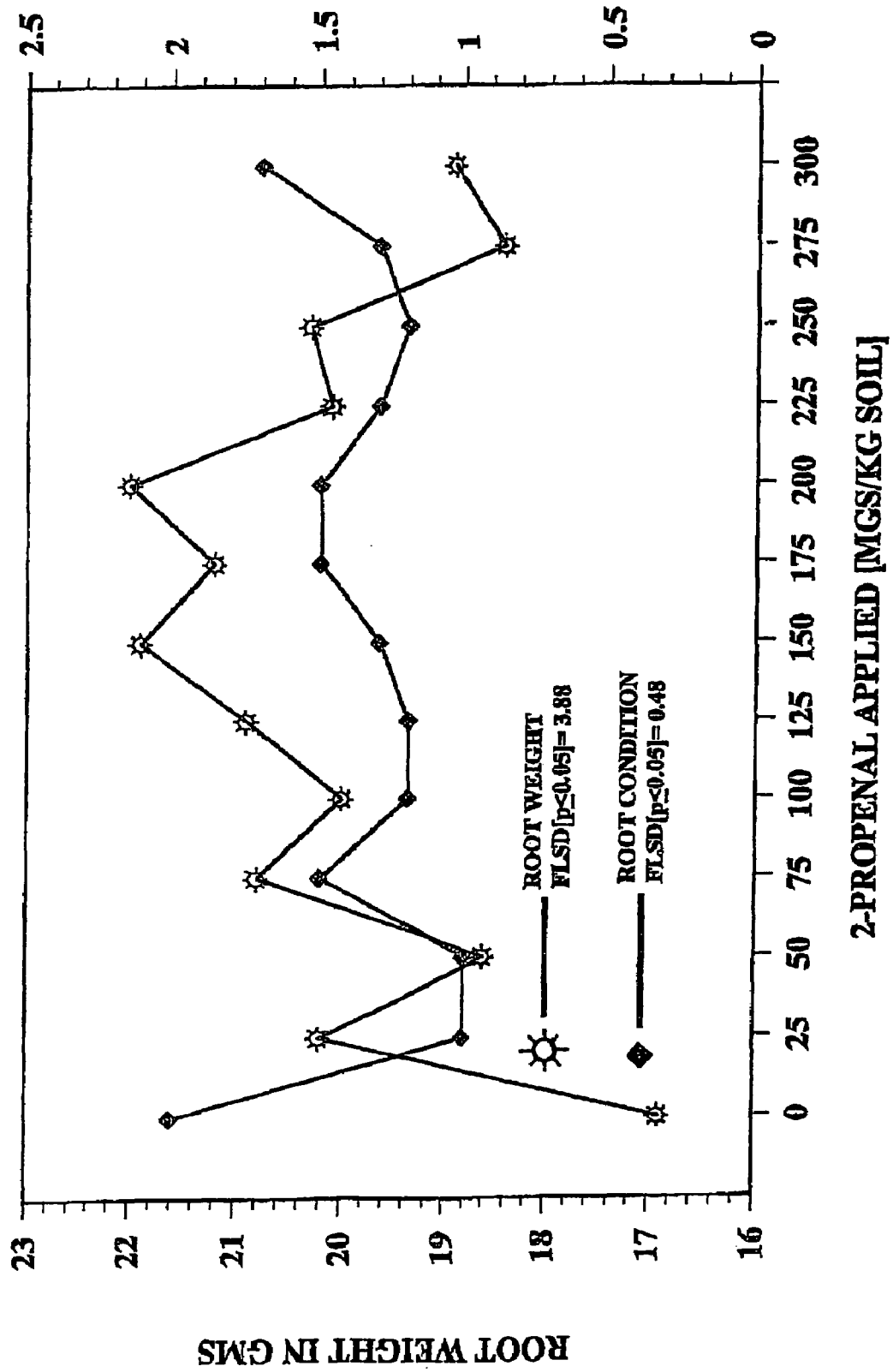
FIG. 2B is a graph illustrating the effect of 2-propenal on the growth response of soybean plants at various pre-emergent application rates on root weight and root condition of the plant.

Sharp increases in shoot height and weights were observed in response to dosages ≦50 mgs (FIGS. 2A-2C); this was followed by gradual decline in values for the two variables. The overall response was typical of a log-normal model. Root weights increased gradually (FIGS. 2D-2E) in response to rates up to 175 mgs and declined with higher dosages in a typical Gaussian symmetrical pattern. Root condition was improved by all but the highest dose of 2-propenal (FIG. 2D).

Figure 3:
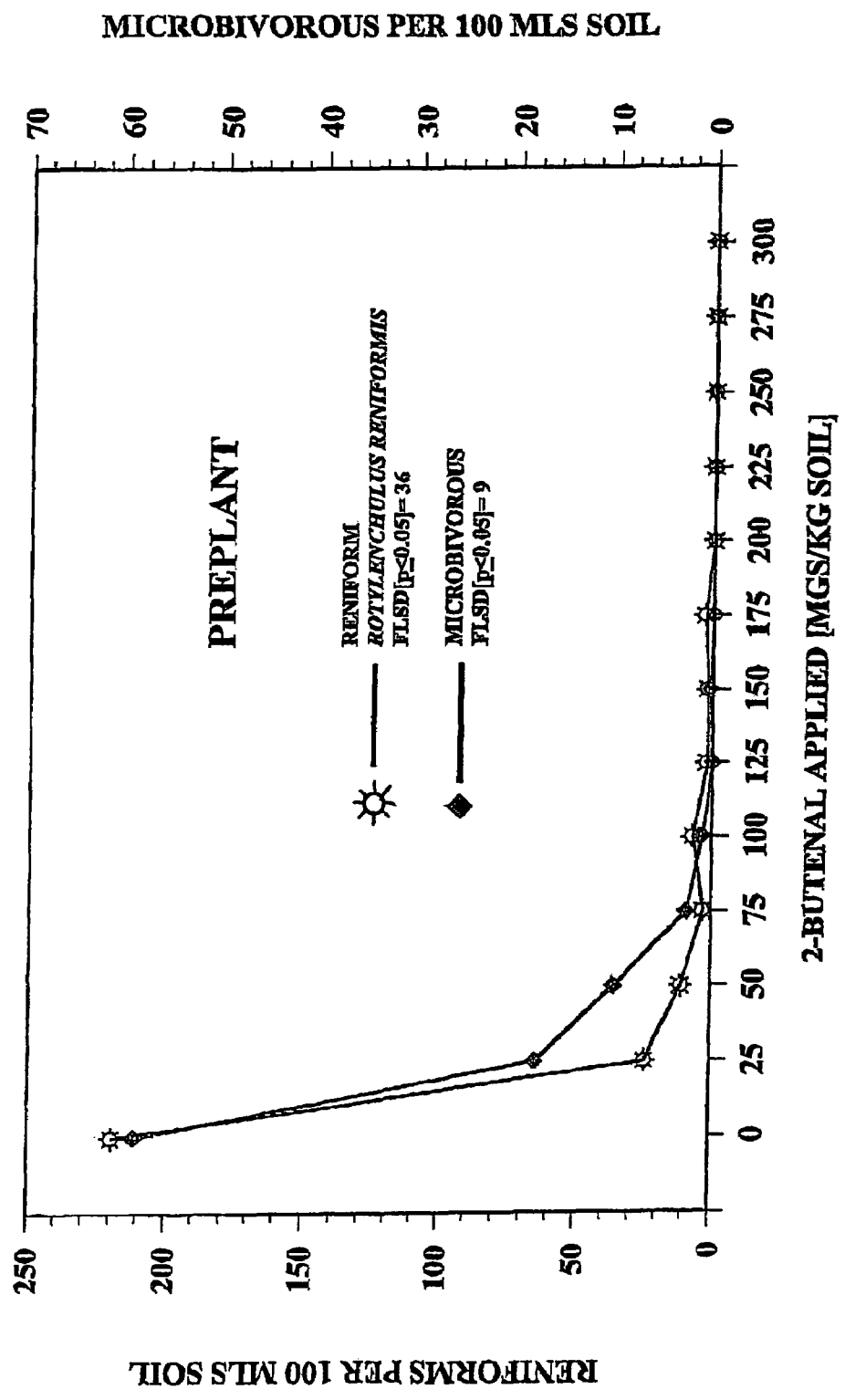
FIG. 3 is a graph illustrating the effect of 2-butenal on reniform and microbivorous nematodes in soil at various pre-emergent application rates.

2-butenal. Response patterns of nematodes to applications of 2-butenal were very similar to those described for 2-propenal. FIG. 3 serve to illustrate the similarity of response between the two compounds.

Figure 6A:
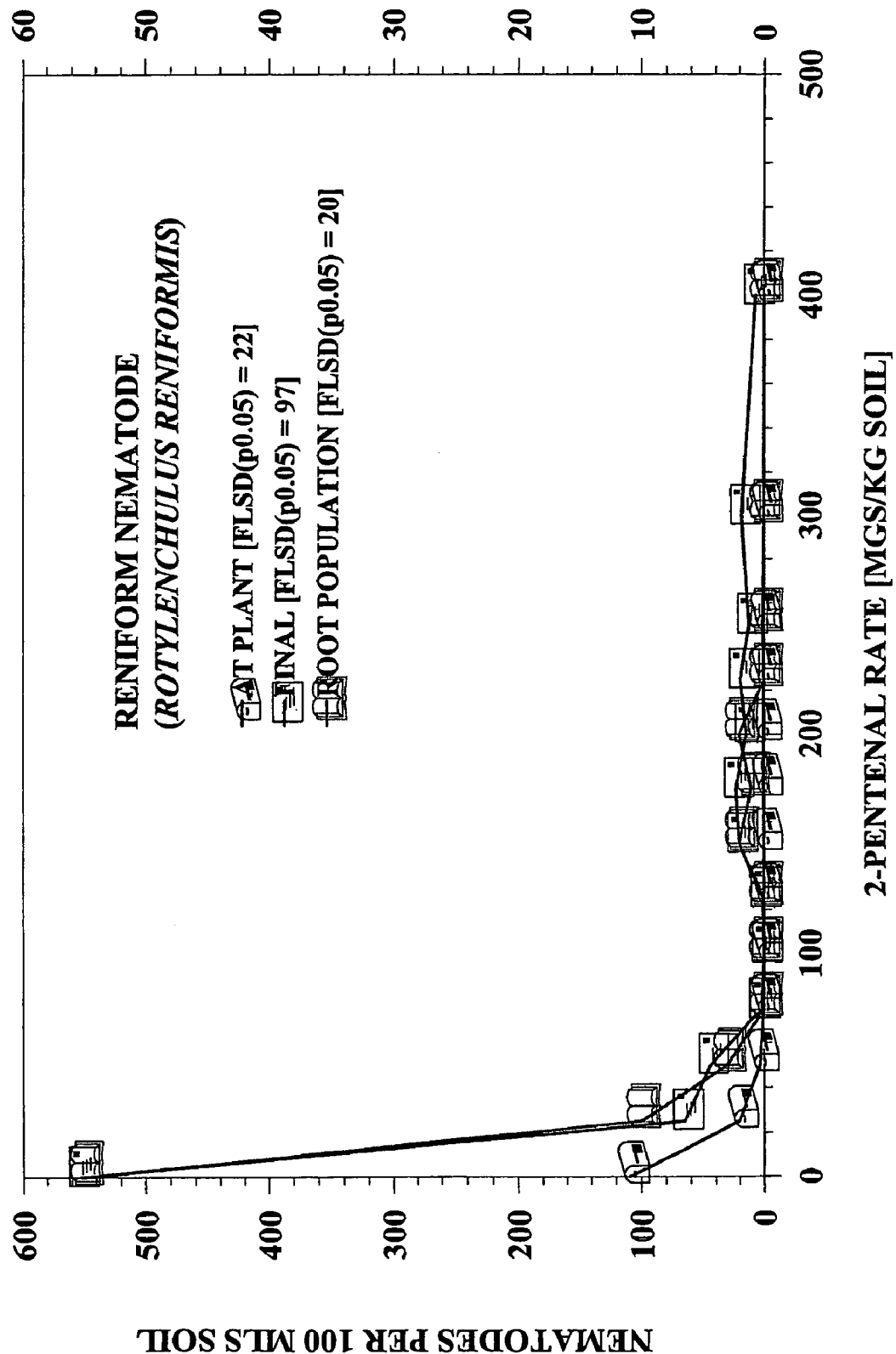
FIG. 6A is a graph illustrating the effect of 2-pentenal on reniform nematodes in soil and roots.
Figure 6B:
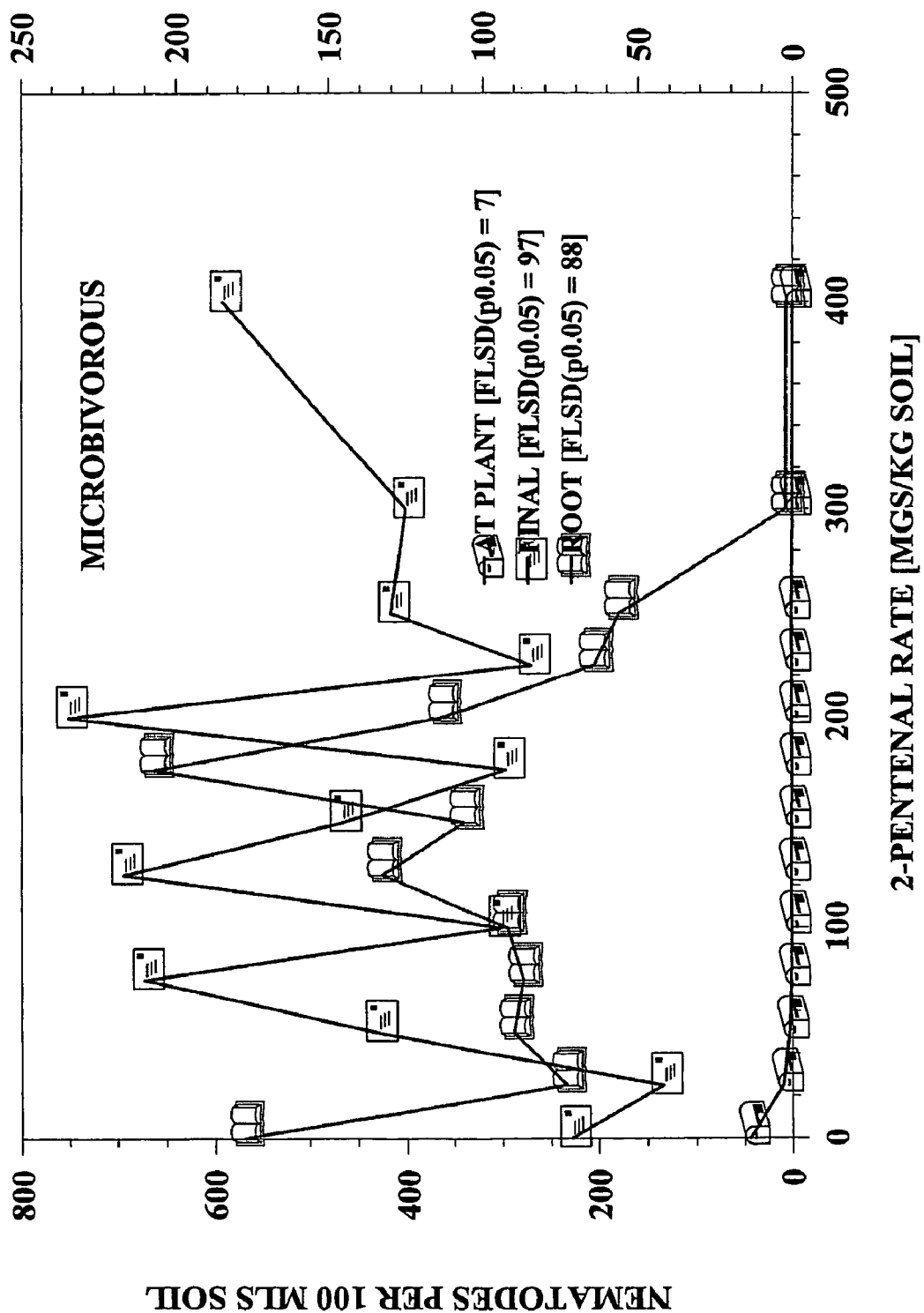
FIG. 6B is a graph illustrating the effective of 2-pentenal on microbivorous nematodes in soil and roots.

2-pentenal. Response patterns of nematodes to applications of 2-pentenal were very similar to those described for 2-propenal. FIGS. 6A-6B serve to illustrate the similarity of responses between the two compounds.

Figure 4:
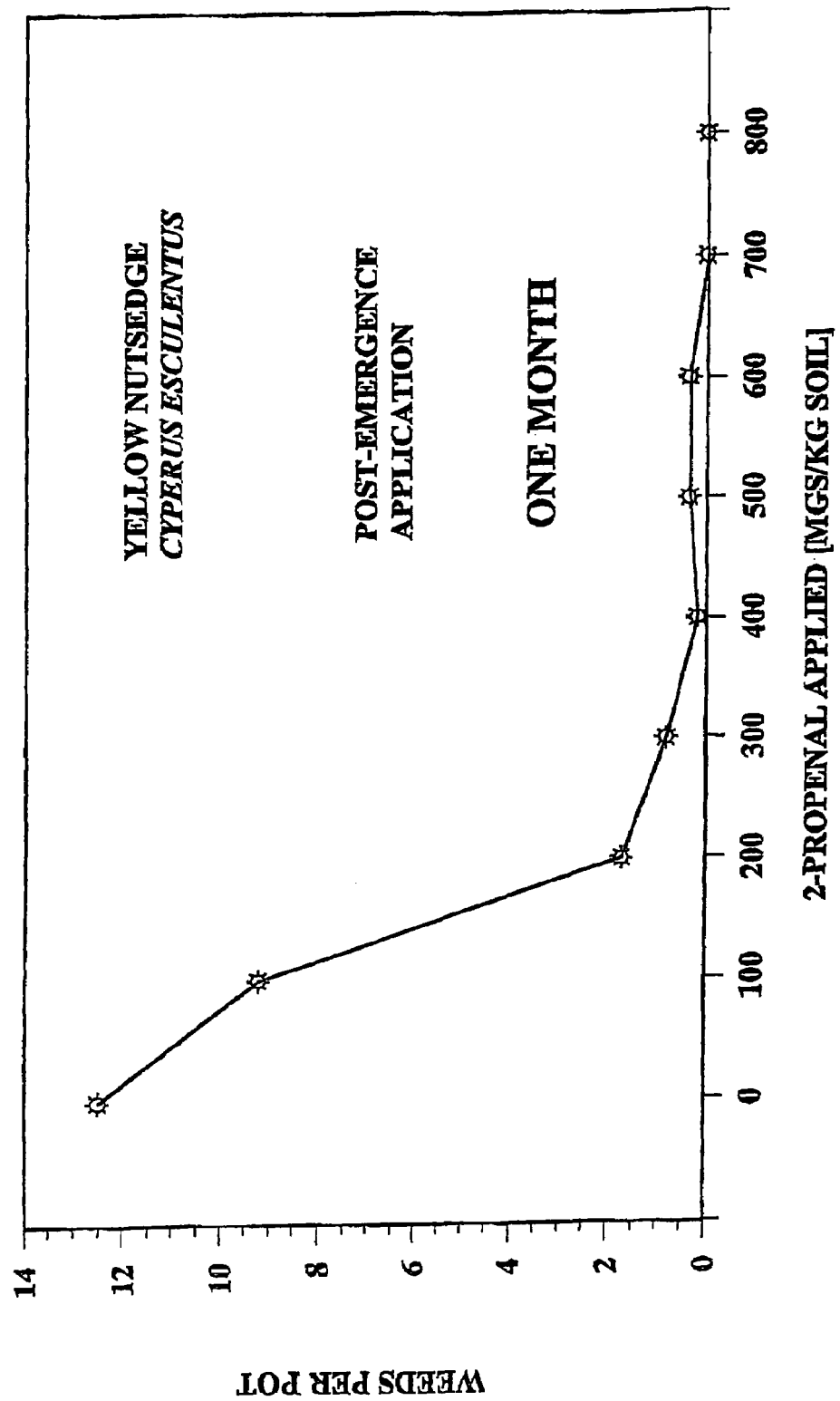
FIG. 4 is a graph illustrating the effect of 2-propenal on yellow nutsedge in response to various post emergent application rates.

Herbicidal Activity. Application of 2-propenal resulted in sharp declines in the number of yellow nutsedge weeds in response to increasing doses of the chemical (FIG. 4). The relation between dose and weed population adjusted well to an inverse cubic model (FIG. 4) indicating that doses ≧200 mgs/kgs soil applied post-emergence resulted in practical elimination of the weed.

Figure 5:
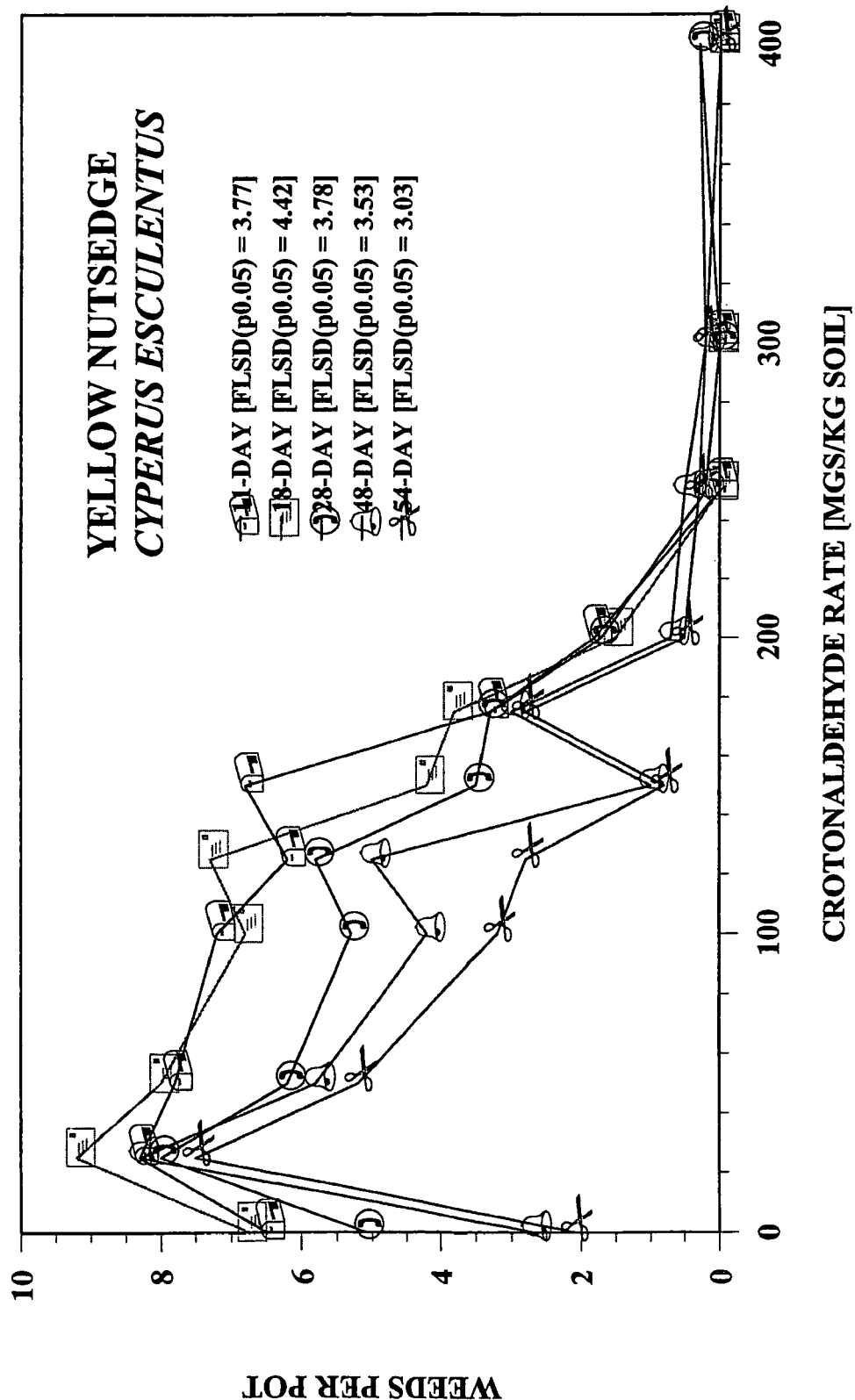
FIG. 5 is a graph illustrating the effect of 2-butenal (crotonaldehyde) on yellow nutsedge in response to various post emergent application rates.

Application of 2-butenal also resulted in sharp declines in the number of yellow nutsedge weeds in response to increasing dose of the chemical (FIG. 5). FIG. 5 thus illustrates the similarity of responses between the two compounds.

Application of 2-pentenal is likewise expected to result in sharp declines in the number of yellow nutsedge weeds in response to increasing doses of the chemical (data not shown).

Conclusions 2-propenal, 2-butenal and 2-pentenal are powerful nematicidal and herbicidal compounds with long-term effects against plant pathogenic nematodes but with no long lasting negative effects on beneficial microbivorous nematodes. Application rates of 50-100 mgs/kg soil which are equivalent to 100-200 lbs/acre (lbs/A) on a broadcast basis eliminate plant pathogenic nematodes, retain microbivorous nematodes and increase growth of plants. Yellow nutsedge, a hard-to-kill species, and other weeds were practically eliminated with rates ≧200 mgs/kg soil; the 200 (mgs/kg) rate is equivalent to 400 lbs/A on a broadcast basis. These rates are very practical and are considerably below those used with methyl bromide (400-1000 lbs/A) for soil fumigation. The fact that 2-propenal and 2-butenal are precursors for the synthesis of many other organic compounds makes these chemicals available in large quantities and at a very reasonable price compared with current prices for methyl bromide.

EXAMPLE 2

This example together with the data in Table 1 includes results of a study conducted to test the affects of acrolein on tomato plant growth. The first column in Table 1 includes, from left to right the treatment number, the treatment name, the rate of application, and the unit for that rate. The treatment name includes two separate treatment ingredients for each treatment number. The top name of each treatment name lists the test additive, and the bottom listing of the treatment name lists any additional herbicide applied in that particular treatment number. For example, in treatment number 5, methyl bromide was applied with a sandea herbicide. The rate and the rate unit headings, for this study, lists the amount of application of the treatment ingredients in pounds of active ingredients per acre (lb ai/a). Column 2 of Table 1 lists a vigor rating for each tomato plant on a scale of 1 to 5, wherein a 1 rating indicates a tomato plant with very little vigor, and a 5 rating indicates a very vigorous tomato plant. Column 2 lists vigor scale ratings for each treatment number taken on Aug. 17, 2005, and column 3 lists a vigor rating for each treatment taken on Aug. 25, 2005. Comparing column 2 to column 3 will illustrate whether any given treatment had a positive or negative effect on the vigor of the tomato plant.

Still referring to Table 1, treatment number 1 shows a "check 1" treatment with no additional herbicide. This treatment is merely a "check" treatment, meaning that neither methyl bromide, nor acrolein were applied to the tomato plant. In treatment 1, the vigor of the tomato plant decreased from 3.5 to 3.0 over the duration of the test. Treatment 4 shows that 350 pounds of active ingredient per acre of methyl bromide 1 was applied to the tomato plant with no additional herbicide, which resulted in no change in vigor scale rating over the term of the test. Treatment numbers 7 and 13 illustrate acrolein injected into the soil with no additional herbicides at relatively low rates of 200 pounds of active ingredient per acre and 400 pounds of active ingredient per acre, respectively. In treatment number 7, the vigor of the tomato plant enjoyed an increase of 4.25 to 4.75, and in test 13, the tomato plant enjoyed an increase in vigor of 4.0 to 5.0. The results included in Table 1 support the conclusion that relatively small amounts of acrolein applied to the soil around tomato plants increase the vigor and stimulates growth of the tomato plants, while applying methyl bromide to the soil around tomato plants results in no significant improvement in vigor and/or growth of tomato plants. At the same time, the untreated tomato plants showed a decrease in vigor scale.

TABLE 1

| Trt No. | Treatment Name | Rate | Rate Unit | TOMATO 17/Aug/05 VIGOR 1-5SCALE 2 | TOMATO 25/Aug/05 VIGOR 1-5SCALE 3 |
|---|---|---|---|---|---|
| 1 | CHECK 1 NONE | | | 3.500 | 3.000 |
| 2 | CHECK 1 SANDEA | 0.25 | lb ai/a | 3.250 | 3.250 |
| 3 | CHECK 1 V-10142 | 0.25 | lb ai/a | 3.000 | 3.500 |
| 4 | METHYL BROMIDE 1 NO HERBICIDE | 350 | lb ai/a | 2.500 | 2.500 |
| 5 | METHYL BROMIDE 1 SANDEA | 350 0.25 | lb ai/a lb ai/a | 2.250 | 2.750 |

TABLE 1-continued

| Trt No. | Treatment Name | Rate | Rate Unit | TOMATO 17/Aug/05 VIGOR 1-5SCALE 2 | TOMATO 25/Aug/05 VIGOR 1-5SCALE 3 |
|---|---|---|---|---|---|
| 6 | METHYL BROMIDE 1 | 350 | lb ai/a | 2.000 | 2.650 |
|  | V-10142 | 0.25 | lb ai/a |  |  |
| 7 | ACROLEIN INJECT NO HERBICIDE | 200 | lb ai/a | 4.250 | 4.750 |
| 8 | ACROLEIN INJECT SANDEA | 200 0.25 | lb ai/a lb ai/a | 4.000 | 4.750 |
| 9 | ACROLEIN INJECT V-10142 | 200 0.25 | lb ai/a lb ai/a | 4.000 | 4.750 |
| 10 | ACROLEIN DRIP NO HERBICIDE | 600 | lb ai/a | 1.250 | 2.500 |
| 11 | ACROLEIN DRIP SANDEA | 600 0.25 | lb ai/a lb ai/a | 1.500 | 2.500 |
| 12 | ACROLEIN DRIP V-10142 | 600 0.25 | lb ai/a lb ai/a | 2.250 | 2.900 |
| 13 | ACROLEIN INJECT NO HERBICIDE | 400 | lb ai/a | 4.000 | 5.000 |
| 14 | ACROLEIN INJECT SANDEA | 400 0.25 | lb ai/a lb ai/a | 3.000 | 4.250 |
| 15 | ACROLEIN INJECT V-10142 | 400 0.25 | lb ai/a lb ai/a | 4.000 | 4.650 |
| 16 | ACROLEIN DRIP NO HERBICIDE | 400 | lb ai/a | 3.000 | 3.250 |
| 17 | ACROLEIN DRIP SANDEA | 400 0.25 | lb ai/a lb ai/a | 2.750 | 3.500 |
| 18 | ACROLEIN DRIP V-10142 | 400 0.25 | lb ai/a lb ai/a | 3.000 | 3.250 |
| 19 | ACROLEIN DRIP NO HERBICIDE | 200 | lb ai/a | 3.000 | 4.000 |
| 20 | ACROLEIN DRIP SANDEA | 200 0.25 | lb ai/a lb ai/a | 3.000 | 3.750 |
| 21 | ACROLEIN DRIP V-10142 | 200 0.25 | lb ai/a lb ai/a | 3.000 | 3.850 |
| 22 | ACROLEIN INJECT NO HERBICIDE | 600 | lb ai/a | 3.250 | 4.250 |
| 23 | ACROLEIN INJECT SANDEA | 600 0.25 | lb ai/a lb ai/a | 3.250 | 4.000 |
| 24 | ACROLEIN INJECT V-10142 | 600 0.25 | lb ai/a lb ai/a | 3.250 | 3.750 |
| 25 | METHYL BROMIDE 2 NO HERBICIDE | 350 | lb ai/a | 2.250 | 2.500 |
| 26 | METHYL BROMIDE 2 SANDEA | 350 0.25 | lb ai/a lb ai/a | 2.500 | 2.500 |
| 27 | METHYL BROMIDE 2 V-10142 | 350 0.25 | lb ai/a lb ai/a | 2.500 | 2.500 |
| 28 | CHECK 2 NO HERBICIDE | 350 | lb ai/a | 3.250 | 3.500 |
| 29 | CHECK 2 SANDEA | 0.25 | lb ai/a | 2.750 | 3.250 |
| 30 | CHECK 2 V-10142 | 0.25 | lb ai/a | 3.000 | 3.250 |

We claim:

1. A method for controlling pests and weeds on or around plants, comprising the steps of:

providing as an active compound trans-2-pentenal having the structure

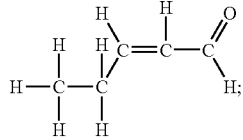

admixing an effective amount of said active compound with water to form an aqueous solution; and applying the aqueous solution to plants, plant seeds, weeds or soil around the area in which the plants grow at a rate that is effective for controlling pests and weeds on or around said plants.

2. The method of claim 1, comprising applying the solution at a rate of about 200 pounds to about 800 pounds of said active compound per acre of soil.

3. The method of claim 1, comprising applying the solution at a rate that is greater than about 400 pounds of said active compound per acre of soil.

4. A method for controlling pests and weeds on or around plants, comprising the steps of:

providing as an active compound 2-butenal having the structure

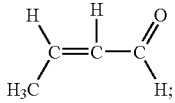

admixing an effective amount of said active compound with water to form an aqueous solution; and applying the aqueous solution to plants, plant seeds, weeds or soil around the area in which the plants grow at a rate of about 200 pounds to about 800 pounds of said active compound per acre of soil.

5. A method for controlling pests and weeds on or around plants, comprising the steps of:

providing as an active compound 2-butenal or trans-2-pentenal:

admixing an effective amount of said active compound with water to form an aqueous solution; and applying the aqueous solution to plants, plant seeds, weeds or soil around the area in which the plants grow at a rate of about 200 pounds to about 800 pounds of said active compound per acre of soil.

6. A method for controlling pests and weeds on or around plants, comprising the steps of:

providing as an active compound 2-butenal or trans-2-pentenal;

admixing an effective amount of said active compound with water to form an aqueous solution; and applying the aqueous solution to plants, plant seeds, weeds or soil around the area in which the plants grow at a rate that is greater than about 400 pounds of said active compound per acre of soil.

7. The method of claim 6, wherein the active compound is 2-butenal.

* * * * *